United States Patent
Thompson

(10) Patent No.: US 6,824,678 B2
(45) Date of Patent: Nov. 30, 2004

(54) CLOSURE SYSTEM FOR CHROMATOGRAPHY COLUMNS

(76) Inventor: Robert D. Thompson, 823 Filley Run, Charlottesville, VA (US) 22903

( * ) Notice: Subject to any disclaimer, the term of this patent is extended or adjusted under 35 U.S.C. 154(b) by 119 days.

(21) Appl. No.: 10/360,382

(22) Filed: Feb. 6, 2003

(65) Prior Publication Data

US 2004/0154969 A1 Aug. 12, 2004

(51) Int. Cl.[7] .............................................. B01D 15/08
(52) U.S. Cl. .................................... 210/198.2; 210/656
(58) Field of Search ................................ 210/635, 656, 210/198.2, 232, 282, 450; 96/101, 105, 106

(56) References Cited

U.S. PATENT DOCUMENTS

| | | | | | |
|---|---|---|---|---|---|
| 3,250,395 | A | * | 5/1966 | Blume | 210/263 |
| 3,826,373 | A | * | 7/1974 | Andreotti | 73/864.84 |
| 4,289,620 | A | * | 9/1981 | Hara | 210/198.2 |
| 4,350,595 | A | * | 9/1982 | Gunkel | 210/656 |
| 4,361,482 | A | * | 11/1982 | Teetz et al. | 210/198.2 |
| 4,604,198 | A | * | 8/1986 | Dailey et al. | 210/198.2 |
| 4,676,898 | A | * | 6/1987 | Saxena | 210/198.2 |
| 4,692,243 | A | * | 9/1987 | Porsch et al. | 210/198.2 |
| 4,710,289 | A | * | 12/1987 | Wermuth et al. | 210/198.2 |
| 4,737,292 | A | * | 4/1988 | Ritacco et al. | 210/656 |
| 4,752,391 | A | * | 6/1988 | Porsch et al. | 210/198.2 |
| 4,755,293 | A | * | 7/1988 | Sakamoto et al. | 210/198.2 |
| 4,797,209 | A | * | 1/1989 | Jackson | 210/656 |
| 4,968,421 | A | * | 11/1990 | Spacek et al. | 210/198.2 |
| 5,213,683 | A | * | 5/1993 | Mann | 210/198.2 |
| 5,282,973 | A | * | 2/1994 | Mann | 210/656 |
| 5,324,427 | A | * | 6/1994 | Traveset-Masanes et al. | 210/198.2 |
| 5,423,982 | A | * | 6/1995 | Jungbauer et al. | 210/198.2 |
| 5,667,676 | A | * | 9/1997 | Alaska | 210/198.2 |
| 5,674,455 | A | * | 10/1997 | Marchand et al. | 422/70 |
| 5,681,474 | A | * | 10/1997 | Gunther et al. | 210/656 |
| 6,132,605 | A | * | 10/2000 | Leavesley et al. | 210/198.2 |
| 6,171,486 | B1 | * | 1/2001 | Green et al. | 210/198.2 |
| 6,576,124 | B2 | * | 6/2003 | Pichl et al. | 210/198.2 |
| 2003/0098280 | A1 | * | 5/2003 | Davis et al. | 210/656 |

* cited by examiner

Primary Examiner—Ernest G. Therkorn
(74) Attorney, Agent, or Firm—William B. Ritchie

(57) ABSTRACT

A closure cap system for glass chromatography columns includes a glass cylinder with unfinished shaping or work on each end, and two sealing caps. The caps have a circumference shoulder with O-rings. The O-rings having the same diameter as the diameter of the glass cylinder unfinished ends. A base and top parts, both containing openings for receiving sealing caps and the glass cylinder. Threaded rods are received by additional openings in said top and base parts. Nuts are affixed at the end of each threaded rod. The combined action of the nuts and threaded rods apply compression forces to the caps and glass cylinder for sealing in a simple and economic manner defining the system as a disposable apparatus.

10 Claims, 6 Drawing Sheets

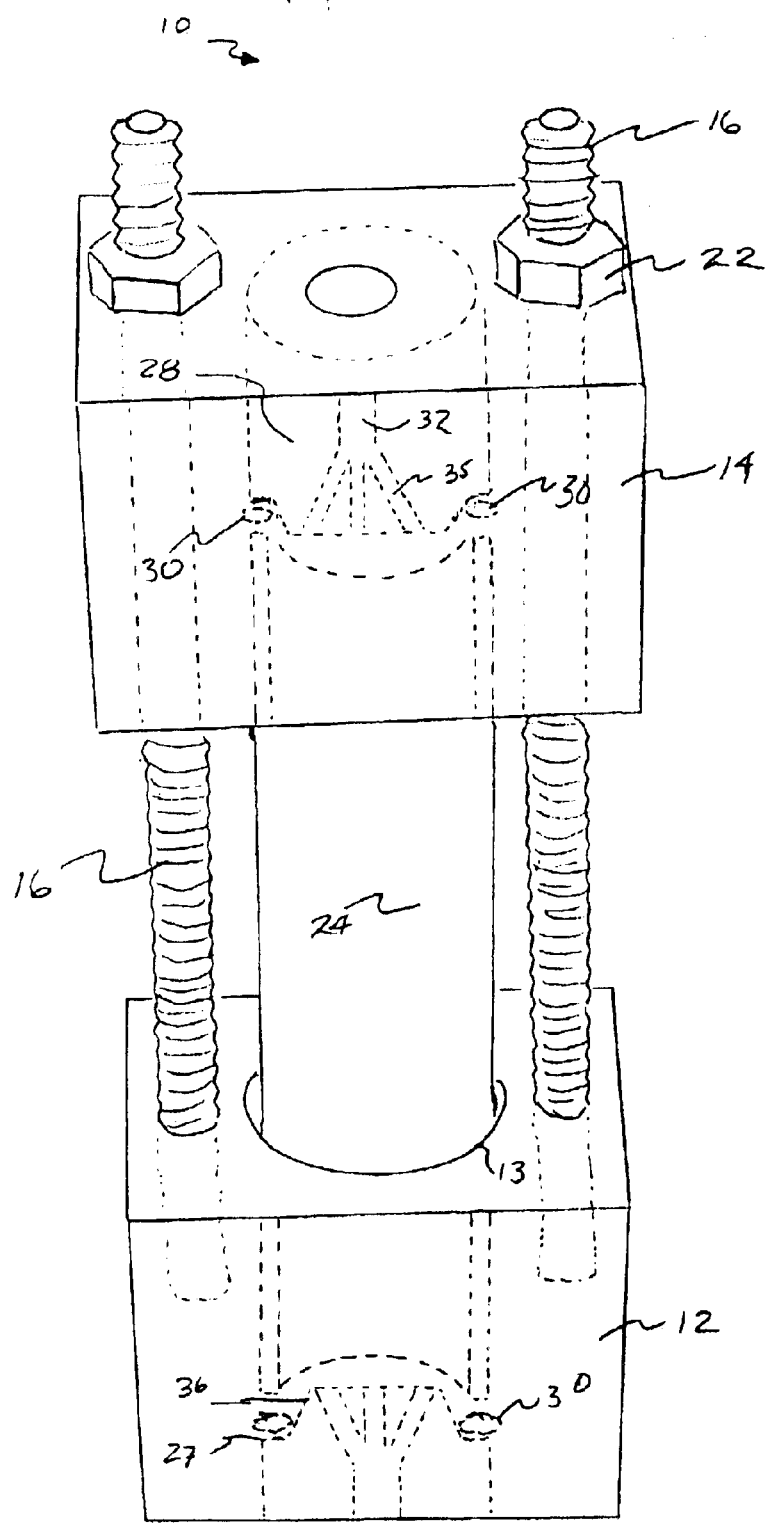

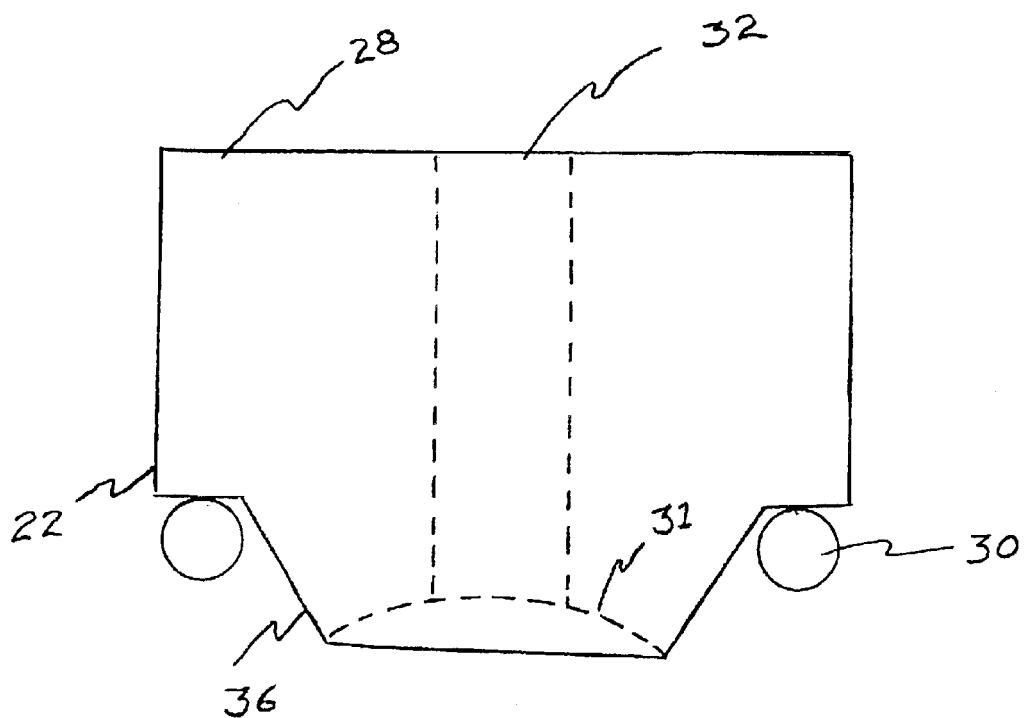

CLOSURE SYSTEM FOR CHROMATOGRAPHY COLUMNS

FIELD OF THE INVENTION

This invention relates to liquid chromatography and, in particular, to disposable glass chromatography columns and apparatus to sealing same.

BACKGROUND OF THE INVENTION

Liquid column chromatography is used for various different purposes. It may be employed to analyze, identify, extract, separate or purify sample components. The typical design consists of a surface-active powder or a size separating material such as a gel product, which is contained in the column. This is called the stationary phase. There is also a mobile phase that consists of a carrier fluid and a sample of the product to be analyzed, identified, extracted, separated or purified.

Liquid chromatography requires the use of different columns designs, depending on the application. Various materials are used in the manufacture of the cylinder used to house the packing media. Metallic cylinders are used to provide columns intended for high-pressure processes. The material most commonly used for the manufacture of this type of column is stainless steel. The columns are pre-packed and sealed with high pressure supporting gaskets. Glass and acrylic or plastic is employed in the manufacture of other cylinder designs.

The disadvantages of metallic columns are related to corrosion. For example, most organic solvents provide satisfactory results. Different results are obtained with long-termed contact with organic acids, halogenated hydrocarbons, and their by-products. Metallic columns are less resistant to the action of aqueous solutions of acids and salts commonly used in the reversed-phase chromatography, ion-exchange chromatography, and affinity and gel chromatography. Changes in the sample may also take place when metal is in contact with mixtures of sensitive biologically active compounds.

As disclosed in U.S. Pat. No. 4,968,421, issued to Spacek et al. on Nov. 6, 1990, glass columns have numerous advantages in liquid chromatography. One important advantage to the use of glass is the high resistance to the action of aggressive mobile phases or separated compounds. The high quality of the inner surface of a glass tube or column is also important because it reduces the spreading caused by the unevenness of the inner surface. This is a problem noted in columns manufactured with plastic materials or the like. The inner surface may suffer deformities and the spreading of the mobile phase becomes uneven. Glass also provides the possibility of visually observing the chromatographic separation and the quality of packing. Plastic columns possess a more opaque color and visualization of the process is not as clear as with a glass cylinder. Further, plastic is substantially less rigid than the glass which prevents or significantly deformation errors.

The disadvantages of glass columns for use in high-pressure chromatography, on the other hand, include the necessity of shaping the glass cylinder for the setting of secure sealing fittings, thus making the use of glass increasingly expensive when compared to other designs and materials. Designs using metallic jackets are complex apparatus and, therefore, do not offer a comparative advantage to steel columns because of cost. Thus, there is presently no disposable glass column that compares favorably in price to the use of plastic columns or steel columns for high-pressure applications.

U.S. Pat. No. 6,171,486 B1, issued to Green et al. on Jan. 9, 2001, discloses a liquid chromatography plastic cartridge with end caps. This invention describes a system that uses clamps, which are circumferentially located about the cartridge wall and seals by applying radial force. This is necessary since the plastic walls are flexible. The invention, as a result of the cylinder being fabricated with plastic, does not overcome difficulties associated with glass columns, nor does it contribute to designing a disposable column for such type of material.

U.S. Pat. No. 6,132,605, issued to Leavesley et al. issued on Oct. 17, 2000, discloses an apparatus for making a sealable connection to a plastic chromatography cartridge. In this invention, the sealing head or cap and its components are sized to fit by sliding into the cartridge. Once the cap and the elastomeric components are situated within the cartridge, axial compression forces on the elastomeric sealing members cause it to expand laterally and press against the cartridge forming a seal. This concept is applied to cartridges and employs a different technique than the present invention. It seals from inside and uses a cartridge as a column. Leavesley et al. does not resolve the issues addressed by the present invention, namely producing an economic and disposable glass column.

As noted above, Spacek et al. discloses a glass chromatography column. But the invention describes a system where the glass column is placed within a jacket. The jacket has threads on its ends and through axial forces closing sockets to seal the column by providing axial forces. The invention by Spacek et al. is not a disposable column since it is not advantageously economical to produce such system for single use.

The prior art does not disclose a closing system applicable to a glass chromatography column, which is simple and economic so as to provide a disposable unit. Moreover, it does not disclose a disposable glass column that compares favorably with the cost of plastic column and yet offers the advantages of glass.

SUMMARY OF THE INVENTION

It is an aspect of the invention to provide a chromatography column that is disposable.

Another aspect of the invention is to provide a chromatography column that utilizes a glass column and has the advantages inherent to such material as noted.

Still another aspect of the invention is provide a chromatography column that can be manufactured without requiring the ends of the glass tube to smooth or otherwise finished, i.e., the glass tube ends are merely rough cut.

It is another aspect of the invention to provide a chromatography column that is sealed with caps that placed under compression.

Another aspect of the invention is to provide a chromatography column that is translucent.

It is another aspect of the invention to provide a chromatography column that has a high chemical resistance.

Still another aspect of the invention is to provide a chromatography column that is assembled with simple made or readily available parts.

It is another aspect of the invention to provide a chromatography column that is readily adaptable to different sizes and packing materials so as to meet most chromatography applications.

Finally, it is an aspect of the invention to provide a chromatography column wherein the sealing caps can be adapted to various manifold configurations so that sorbents can be distributed evenly over the stationary phase materials contained within the column.

These and other aspects of the invention will become apparent in light of the detailed description of the invention which follows.

The invention is a disposable chromatography apparatus. A glass cylinder having top and bottom unfinished ends and internal diameter is provided. A top sealing cap having a sealing diameter and an integral manifold is provided. A top O-ring that is adapted to seal the top unfinished end of said glass cylinder is provided. A bottom sealing having an outlet and a sealing diameter is also provided. A bottom O-ring that is adapted to seal the bottom unfinished end of said glass cylinder is also provided. Wherein inserting said top sealing cap on the top unfinished end and inserting said bottom sealing cap on the bottom unfinished end and placing said caps under a compressive force so that said O-rings are urged against their respective unfinished ends, said apparatus is sealed.

BRIEF DESCRIPTION OF THE DRAWINGS

FIG. 1 is a cross-section view of the chromatography column according to the invention.

FIG. 3 is a cross-sectional view of alternative cap design.

DESCRIPTION OF THE PREFERRED EMBODIMENTS

Figure 2A:
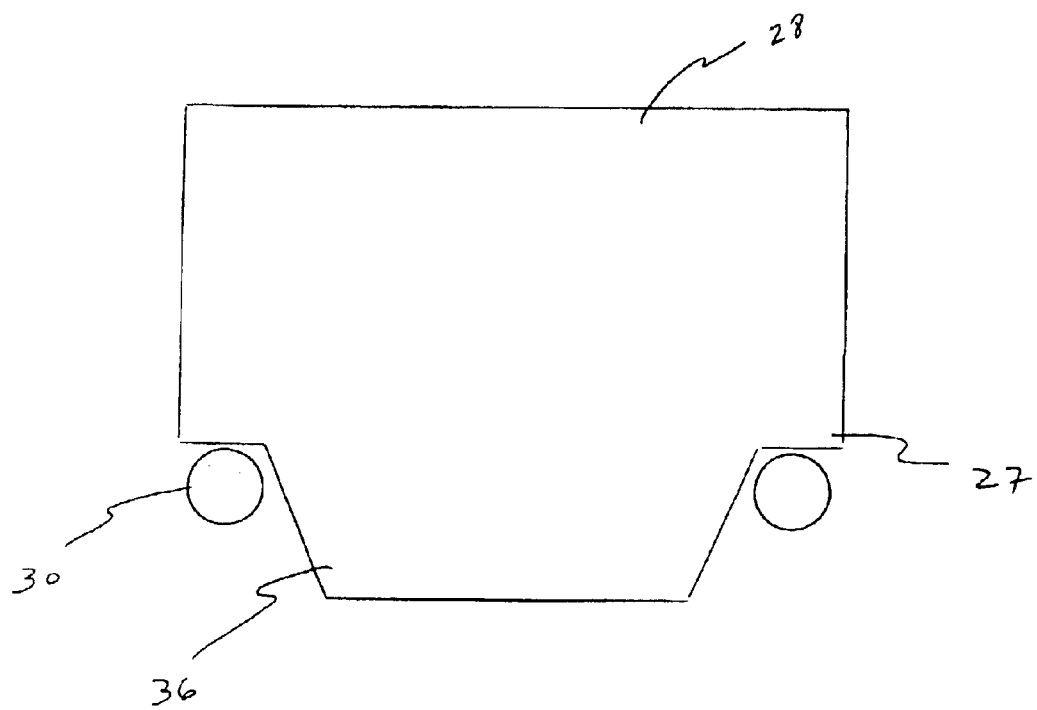
FIG. 2 is a cross-section view of the cap sealing design of the invention.

The invention uses a closing system that permits having a glass cylinder having no finishing, machining or shaping work at each end. Using glass cylinders with unfinished ends, as provided after the cylinder has been cut to length, reduces significantly the cost of manufacturing. The closure is provided by end caps having O-rings that will seal the apparatus during use. Several types of O-rings are suitable depending on the solvent that is being used. A Buna-N O-ring works well with aliphatic hydrocarbons, oils and water. A VITON O-ring is useful when working with alcohols, aliphatic hydrocarbons, chlorinated hydrocarbons, oils, water, basic solutions, and ammonia. A silicone O-ring works well with alcohols, oils, waster basic solutions and ammonia. Ethylene-propylene polymer (FETFE) O-rings are suitable for water, basic solutions and acidic solutions. CAPFE (a silicon encased in TPFE (a fluoro polymer such as TEFLON as made by DuPont)) O-ring is the preferred choice for alcohols, aliphatic hydrocarbons, chlorinated hydrocarbons, oils, water, basic solutions, ammonia, acidic solutions, ketones, esters, and aldehydes. KALREZ, CHEMRAZ, White Seal have not been tested but it is expected that these will also work with materials useful with the CAPFE O-ring. All of these O-rings are readily available from companies such as ACE Glass, Inc., McMaster Carr, and US Hydraulics.

The closing system has two end caps containing O-rings that seal against the top of the glass cylinder when the two end caps are place under compression.

The disposable nature of the column permits pre-packing with sorbents or stationary phase materials. This reduces labor and costs in chromatography operation. The glass cylinder may be pre-packed with chromatography media in a ready-to-use configuration, only available to date in steel and plastic columns.

The column is easily assembled. A base and top parts are provided for the insertion of the sealing caps and the glass cylinder. The base and top have openings for receiving the sealing caps and the cylinder. Two rods secure the base and top parts and also provide compression for the caps to seal.

The caps, as well as the base and top parts, can be easily removed from the glass cylinder so that said glass cylinder may be re-used by packing new stationary phase materials. Thus, the invention could be used as a disposable column or re-used in chromatography processes.

In operation, the closing caps having O-rings are inserted onto a rough cut glass cylinder with unfinished ends. Once the O-rings contact the unfinished diameter border of the glass cylinder, the caps and glass cylinder are inserted into openings in the base and top parts. The rods are passed through side openings of the base and top parts and nuts inserted on the rods end that are threaded. Compression between the top and base parts effected by the action of the nuts in the threaded rods cause caps to seal the glass cylinder inserted in between the top and base parts.

Referring to FIGS. 1–5, invention 10 is filly assembled. A glass cylinder 24 with unfinished ends 26 is provided. While preferably, cylinder 24 is made from glass, it is also possible to use steel for those circumstances where steel or other such material is more beneficial. Cylinder 24 may be pre-packed with sorbents or stationary phase materials 34 and become disposable after use. For such purpose, the invention features a cap 28 having a circumference shoulder 27 that corresponds to the diameter 29 of the glass cylinder 24. On the circumference shoulder 27 of the cap 28 is an O-ring 30 having a diameter that corresponds to the diameter 29 of the glass cylinder 24 so that the O-ring 30 seals cap 28 where in cap 28 is in contact with said cylinder 24. The cap 28 may include a protruding or extending shape form 36. Around the extended shape 36 in the cap 28 is the circumference shoulder 27 with the O-ring 30. This design limits the dead volume between the cap 28 and the stationary phase materials 34 in the column, thus permitting a more efficient chromatography process. The cap 28 contains a single inlet 32 of fluid and a manifold outlet 35, which evenly disseminates the fluid into the glass cylinder 24. While the preferred embodiment is disposable, the caps, base and even the cylinder may be re-used if so desired.

Several options are possible for manifold outlet 35. One embodiment has six openings each at approximately 45 degrees in relation to the axis of cylinder 24. However, other configurations are also suitable such as a single opening or variations of multiple openings with even greater number of openings than six.

The glass cylinder 24, with the cap 28 positioned as described above, sits on a rectangular base 12 having a round opening 13. Through this opening 13, the glass cylinder 24 and the sealing cap 28 are inserted until stopped by a bottom part 15 in said opening 13. This bottom part 15 has an outlet 11 for the passage of connecting tubing to the glass cylinder 24 through the cap 28. A top part 14 has another cylinder and cap-receiving opening 17. The other end of the cylinder 24 and the corresponding cap 28 are inserted in the same manner as described above for the base 12.

While caps 28 for base 12 and top part 14 are shown as being essentially identical, that does not have to be the case.

Cap 28 for the top part 14 could have multiple opening manifold 35 as shown while cap 28 for the base could be a single conical shaped opening on the bottom surface.

Additionally, both the base 12 and top 14 parts feature openings 18 for rods 16. The rods 16 are inserted in base openings 18, and have sufficient length to reach the top part 14. The top part 14 has essentially the same configuration as the base part 12. The rods 16 are received in the top part 14 by openings 20. These openings 20 are situated next to the openings 13 and 17 for the glass cylinder and the caps 28. Once the caps 28 and the glass cylinder 24 are inserted into the base and top openings 13 and 17, sliding until stopped by the bottom part 15 in the openings, the threaded rods 16 are also inserted into the corresponding openings 18 and 20, and nuts 22 are affixed and used for compression in the closure of the glass cylinder 24. While nuts 22 are shown as typical hexagonal nuts, other fastening means well known in the art would also suffice. Further rods 16 are shown threaded from top to bottom; however, threading only the end portions of rods 16 would be acceptable.

Figure 2B:
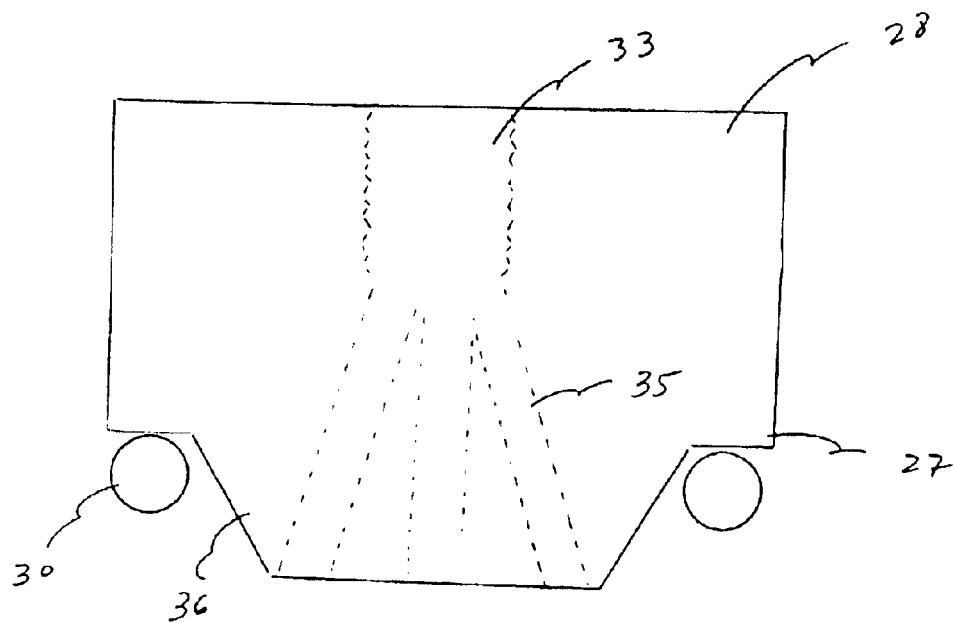

FIGS. 2a and 2b show a cross-section of the sealing cap 28. A circumference shoulder 27 holds an O-ring 30 positioned to contact the diameter 29 of the glass cylinder 24. The cap 28 has an extended shape 36. In operation, when the O-ring 30 contacts the unfinished end 26 of the glass cylinder 24, the extended bottom part 36 of the cap 28 situates inside the glass cylinder 24, limiting dead volume between chromatography media 34 and the sealing cap 28.

The preferred embodiment for sealing cap 28 is shown in FIG. 3, as noted above, while the inlet may have various outlets in manifold configuration 35, single outlet 32 is preferred. In this embodiment, the mobile phase fluid is more evenly spread into the chromatography media 34 via conical shaped recess 31.

In another embodiment as shown in FIGS. 2a, 2b, the manifold outlet 35 allows even spreading of the mobile phase fluid into the chromatography media 34 in the glass cylinder 24. As shown in FIG. 2b, inlet 33 may be threaded to permit a secure connection between inlet 32 and tubing typically used for carrying or collecting mobile phase fluids into the column.

Figure 4A:
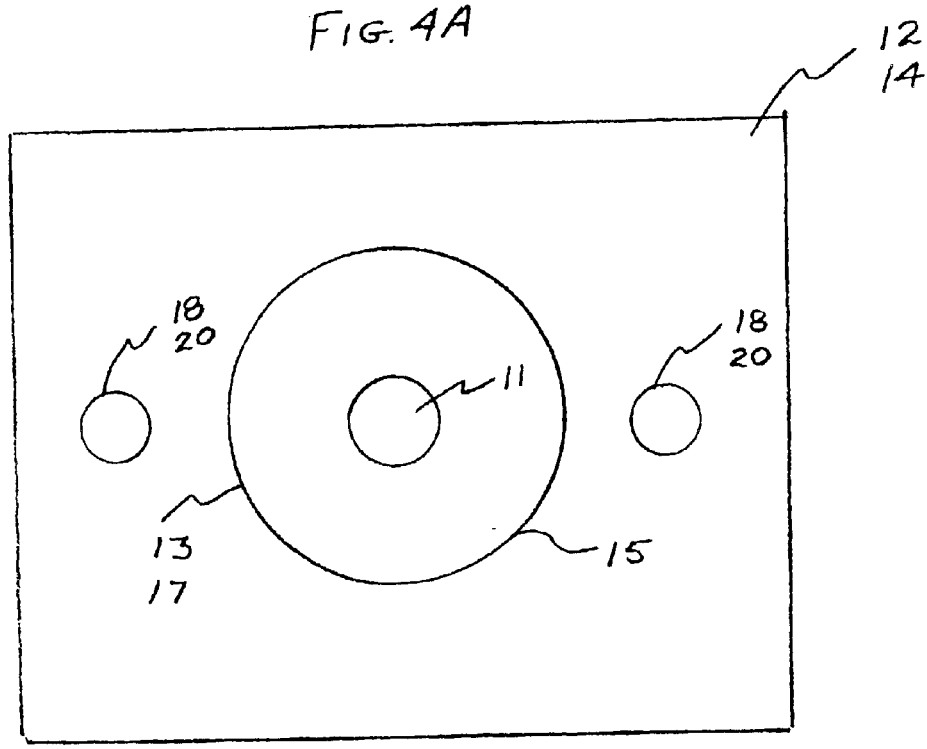
FIG. 4a is a bottom view of the base.
Figure 4B:
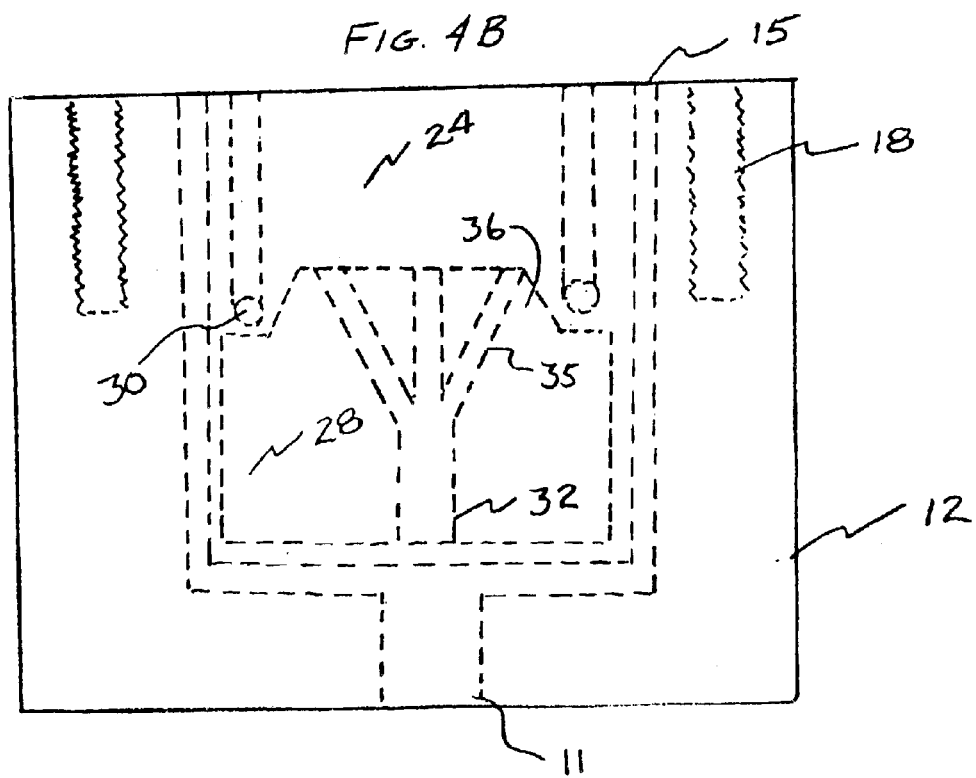
FIG. 4b is a side view of the base showing the glass column being sealed with a cap therein.
Figure 5:
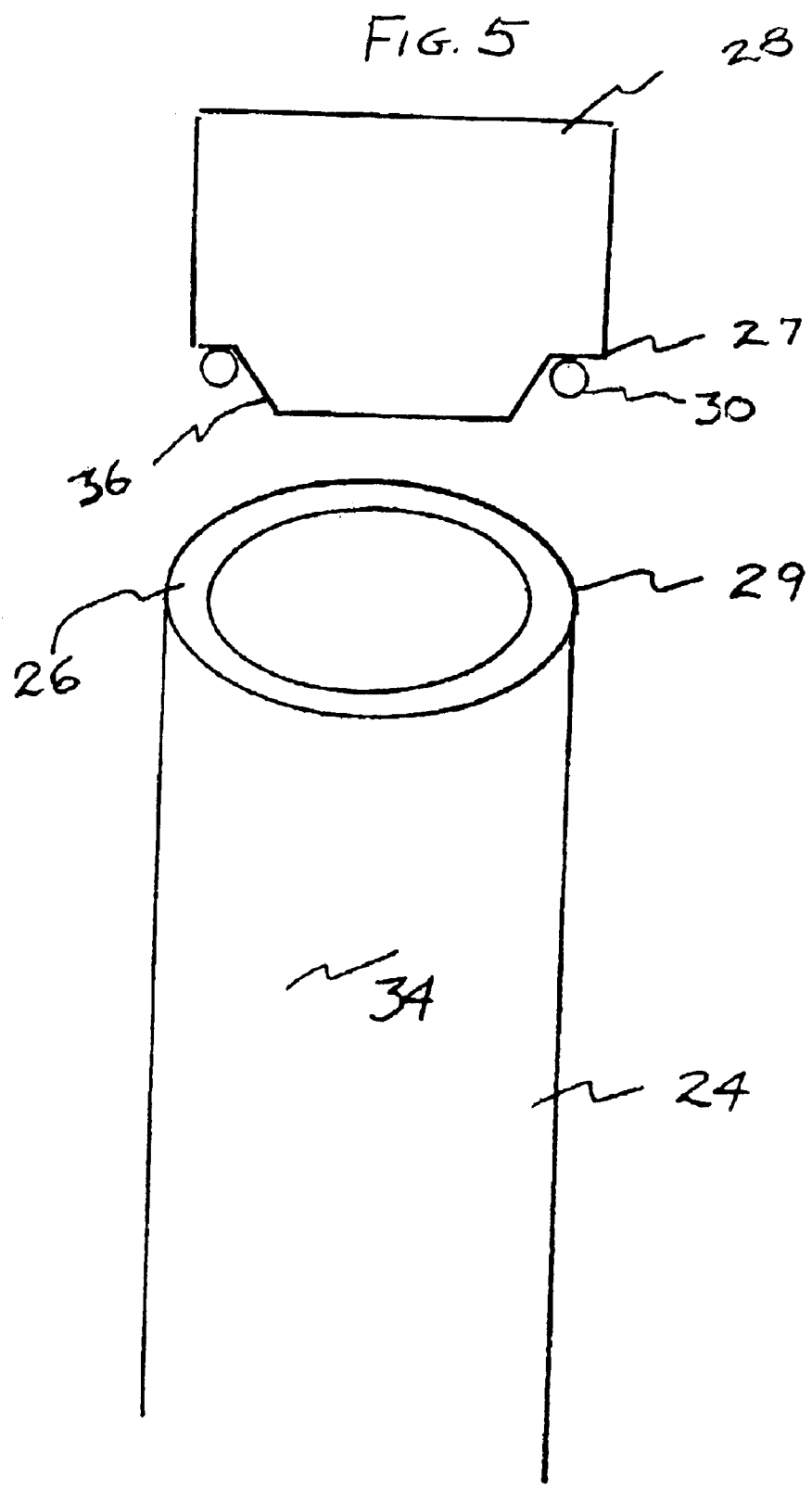
FIG. 5 is a detailed isometric view of the cap sealing a glass tube.

Referring to FIG. 4, the top and base parts 12 and 14 contain openings 13 and 17 for receiving the sealing caps 28 and the glass cylinder 24. Each said opening 13 and 17 possesses a bottom part 15 so that the sealing cap 28 and glass cylinder 24 remain in place not sliding through said openings 13 and 17. Moreover, this bottom part 15 allows compression to effectively seal the cylinder 24. As shown in FIG. 4, the bottom part 15 comprises an opening 11 for passage of connecting tubing carrying mobile phase fluids to the column 24 through the sealing cap inlet 32.

The glass cylinder may be constructed of any glass well known in the art that is used for such purposes. Further, the diameter of the glass, wall thickness, and height can be varied in accordance with the typical uses as is also well known the art.

The threaded rods 16 may be made of steel or other material having suitable strength to hold the apparatus together during use.

Figure 6:
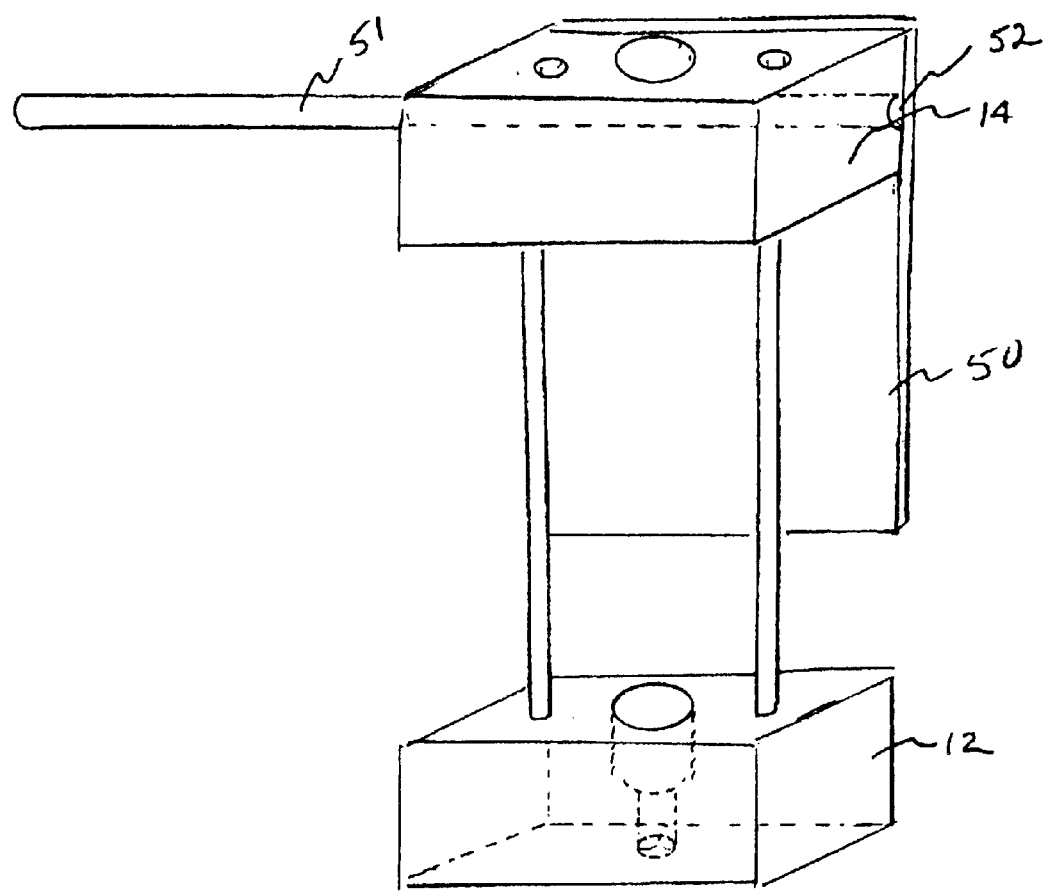
FIG. 6 is an alternative embodiment of the invention.

As shown in FIG. 6, top part 14 may be fitted with slot 52 so that support rod 51 can be placed therein. Support rod 51 can then be attached to a stand (not shown) that is well know in this field so that invention 10 cannot be tipped over during use. Attachment plate 50 is optionally provided so that the invention can be easily moved up and down on the stand via keyholes and screws well known in the art (not shown).

While certain representative embodiments of the invention have been described herein for the purposes of illustration, it will be apparent to those skilled in the art that modification therein may be made without departure from the spirit and scope of the invention.

What is claimed is:

1. A glass chromatography apparatus comprising a cylinder having a diameter and having two unfinished ends with each end having a cut surface;

two sealing caps with each cap having circumferential shoulder wherein the circumferential shoulder corresponds to the unfinished ends of said glass cylinder;

two O-rings having a diameter corresponding to the diameter of said glass cylinder and a thickness corresponding to the cut surfaces of the unfinished ends;

a base and a top part having openings for receiving the two sealing caps and said cylinder;

at least one rod extending from the base to top parts;

wherein apparatus is assembled by inserting said sealing caps on each end of said cylinder such that each of said O-rings contacts cut surfaces of said cylinder and circumferential shoulder of said cap wherein assembled cylinder is then inserted into the openings of the base and top parts and said at least one rods is positioned between said base and said top part to draw said base and top part together, thus causing said O-rings to provide a seal between the cut surfaces of the unfinished ends of said cylinder and said caps.

2. The apparatus in claim 1, wherein the sealing cap possesses a threaded inlet connecting tubing for passage of fluids into and through the column.

3. The apparatus in claim 1 wherein said cylinder is glass.

4. The apparatus in claim 1 wherein said O-rings are silicon encased with a fluoro polymer.

5. The apparatus in claim 1 wherein said sealing caps have a passageway within each cap so that a mobile phase fluid may be introduced and removed from said cylinder.

6. The apparatus of claim 5 wherein the passageway of each cap has a single inlet and a single outlet.

7. The apparatus of claim 6 where in the single outlet of each cap exits from a concave surface from said top cap to assist in spreading the mobile phase fluid within the cylinder.

8. The apparatus of claim 5 wherein the passageway of each cap has a single inlet and multiple outlets.

9. The apparatus of claim 5 wherein one of said caps has a passageway with a single inlet and a single outlet and wherein the other of said caps has a passageway having multiple inlets and a single outlet.

10. The apparatus of claim 5 wherein one of said caps has a passageway having a single inlet and a single outlet and wherein the other of said caps has a passageway having multiple inlets and a single outlet.

* * * * *